United States Patent [19]
Jozwiak

[11] Patent Number: 5,770,058
[45] Date of Patent: *Jun. 23, 1998

[54] CENTRIFUGAL SEPARATOR

[75] Inventor: Todd M. Jozwiak, Benton Harbor, Mich.

[73] Assignee: Whirlpool Corporation, Benton Harbor, Mich.

[21] Appl. No.: 713,488

[22] Filed: Sep. 13, 1996

Related U.S. Application Data

[60] Provisional application No. 60/005,365 Oct. 17, 1995.

[51] Int. Cl.⁶ .................................................. B01D 21/26
[52] U.S. Cl. ........................ 210/167; 210/171; 210/173; 210/295; 210/360.1; 210/380.1; 134/104.1; 134/104.4; 134/111; 134/115 G; 241/46.012; 494/36; 494/43
[58] Field of Search ............................. 210/360.1, 380.1, 210/171, 173, 167, 295; 241/46.012; 494/36, 43; 134/104.4, 104.1, 111, 115 G

[56] References Cited

U.S. PATENT DOCUMENTS

| | | |
|---|---|---|
| 1,583,236 | 5/1926 | Murrish . |
| 3,322,285 | 5/1967 | Lopp . |
| 3,575,185 | 4/1971 | Barrbulesco . |
| 3,669,132 | 6/1972 | Mamrose . |
| 3,989,054 | 11/1976 | Mercer . |
| 4,038,103 | 7/1977 | Grunewald . |
| 4,039,452 | 8/1977 | Fernandez . |
| 4,150,679 | 4/1979 | Cushing et al. . |
| 4,297,210 | 10/1981 | Delfosse . |
| 4,319,599 | 3/1982 | Dingler et al. . |
| 4,346,723 | 8/1982 | Geiger . |
| 4,347,861 | 9/1982 | Clearman et al. . |
| 4,392,891 | 7/1983 | Meyers . |
| 4,559,959 | 12/1985 | Meyers . |
| 4,673,441 | 6/1987 | Mayers . |
| 4,971,518 | 11/1990 | Florin . |
| 4,972,861 | 11/1990 | Milocco et al. . |
| 5,097,855 | 3/1992 | Martinsson et al. . |
| 5,165,433 | 11/1992 | Meyers . |
| 5,333,631 | 8/1994 | Kirkland et al. . |
| 5,345,957 | 9/1994 | Cooper et al. . |

FOREIGN PATENT DOCUMENTS 1352655  5/1974  United Kingdom .

Primary Examiner—David A. Reifsnyder
Attorney, Agent, or Firm—Hill & Simpson

[57] ABSTRACT

A centrifugal soil separator for a dishwasher having a rotating centrifuge connected for rotation with a centrifugal impeller, the centrifugal impeller providing a majority of recirculating wash water for the dishwasher while the centrifuge accepts a second portion of flow and spins that portion of flow for soil separation and to achieve a pumping action to move that quantity of water to the wash water delivery system with the quantity of water moved by the centrifugal impeller. By a coordinated stopping, reversing and starting action of the centrifuge, soil collected therein can be disposed to a soil sizing and drain apparatus for flushing and draining the centrifuge.

15 Claims, 3 Drawing Sheets

CENTRIFUGAL SEPARATOR

This application claims the benefit of U.S. Povisional Application No.: 60/005,365 filed Oct. 17, 1995.

BACKGROUND OF THE INVENTION

The invention relates to dishwashers, in particular to food soil separation and disposal mechanisms.

Many commercially available dishwashers utilize centrifugal forces generated by the dishwasher pump to provide for soil separation, and further rely on settling chambers or filters to contain the soils. U.S. Pat. No. 5,165,433 for example discloses such a system.

In that patent, an accumulator annular wall is provided around an annular pump chamber wall. Water is permitted to flow over the pump chamber wall into an annular slot area defined between the walls. An orifice through the accumulator wall allows water and soil to exit this annular slot area into an accumulator or settling area. A screen covering that area allows water to exit upwardly into the dishwasher area while soil is retained in the sump area to be disposed at timed intervals.

Such systems have the drawbacks of keeping filters free flowing or preventing disturbances in settling areas. To solve those problems, typically extra water is required in the form of back flush nozzles or large volume settling tanks. It is advantageous however to reduce water consumption and thereby conserve energy.

SUMMARY OF THE INVENTION

It is an object of the present invention to reduce energy and water consumption or storage in a dishwasher soil separation and disposal system. It is an object of the present invention to provide a soil separation system which does not require fine filtering elements or large settling tanks. It is an object of the present invention to provide a soil separation and disposal system which prevents accumulation of particles on dishes during a wash cycle. It is an object to provide a system which does not require water flow to back flush filters or screens.

The objects of the invention are achieved in that a centrifugal separator is provided which separates and contains soil particles without the need for a settling tank or fine filtering screens. The system also provides soil "sizing" (grinding or size reduction) and a drain system. A pump housing provides a coarse particle screen, flow gathering and redirection channels and additional soil separation means.

The centrifugal separator functions on the principle that a spinning column of water with different diameters at each end will pump water axially. Such a spinning column will also be acted upon by centrifugal forces. As soiled water is pumped through the separator, the centrifugal forces separate food soils based on their densities. Heavier than water soils collect on the outer wall and lighter than water soils collect in the center. By properly controlling the exit, "clean" water can be allowed to escape leaving the soils trapped.

To dispose trapped soils, the spinning column of water is stopped. Some of the "heavy" food soils are allowed to fall out of the column at this time. By reversing the spinning direction and activating the drain system, the water will be pumped out of the dishwasher. Due to the shape of the centrifuge, a significant amount of water and possible food soils are still contained and suspended in the separator after the unit has been pumped dry. By again stopping the motor, the remaining water and soils will fall out of the system below the inlet of the separator. At this point, the pump is again spun in the drain direction to complete the system draining.

Alternatively, disposing of water and food soils may be achieved by either stopping or agitating the separator while allowing a second, smaller pump to draw the soil and water from the unit.

Stopping and starting the system presents a disadvantage in that the system attempts to pump at a high rate during start up. With a large exit opening, this high rate can empty much of the soil that was trapped and dispose it on the dish load or plug spray arm nozzles. To correct this problem, a ring of holes on the centrifuge exit are used in place of an open hole or band. By controlling the number and size of the holes, both the flow rate and soil particle size can be regulated during start-up and normal operation.

Attached to the separator is a centrifugal impeller. Because the separator is designed to pump at a relatively low flow rate, a centrifugal impeller serves to provide the main pumping action for the dishwasher. The impeller draws its water through a coarse mesh screen which prevents large food soils from plugging the water delivery system. This coarse mesh may be configured in many different ways to allow either automatic or manual cleaning.

The impeller can also aid soil separation by adding a soil concentration wall similar to that used in U.S. Pat. No. 5,165,433. This wall allows soil concentrations to be increased and fed to the separator for containment and eventual disposal.

Both the water from the impeller and the separator converge at the outer upper edge of the separator. Here, the spinning water is gathered and redirected by a diffuser to supply the water feed system to the water delivery arms within the dish compartment.

DETAILED DESCRIPTION OF THE PREFERRED EMBODIMENTS

Figure 1:
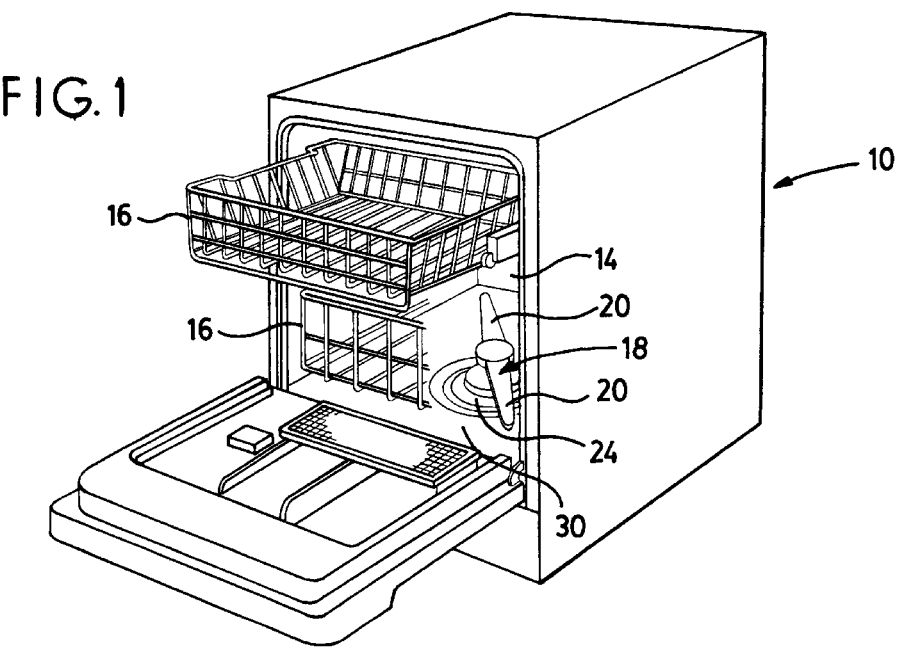
FIG. 1 is a perspective view of a dishwasher using the soil separating system of the present invention.

FIG. 1 illustrates a dishwasher 10 having a dish compartment 14 holding racks 16 for holding dishes, as is known. At a bottom of the dish compartment 14 is a rotary water delivery mechanism 18 including water wash arms 20. The delivery mechanism 18 is mounted on top of a soil separator 24 via a water conduit 26 which feeds water to the delivery mechanism 18 (shown in FIG. 2). An upper wash arm can also be provided and flow connected to the separator 24 (not shown).

Figure 2:
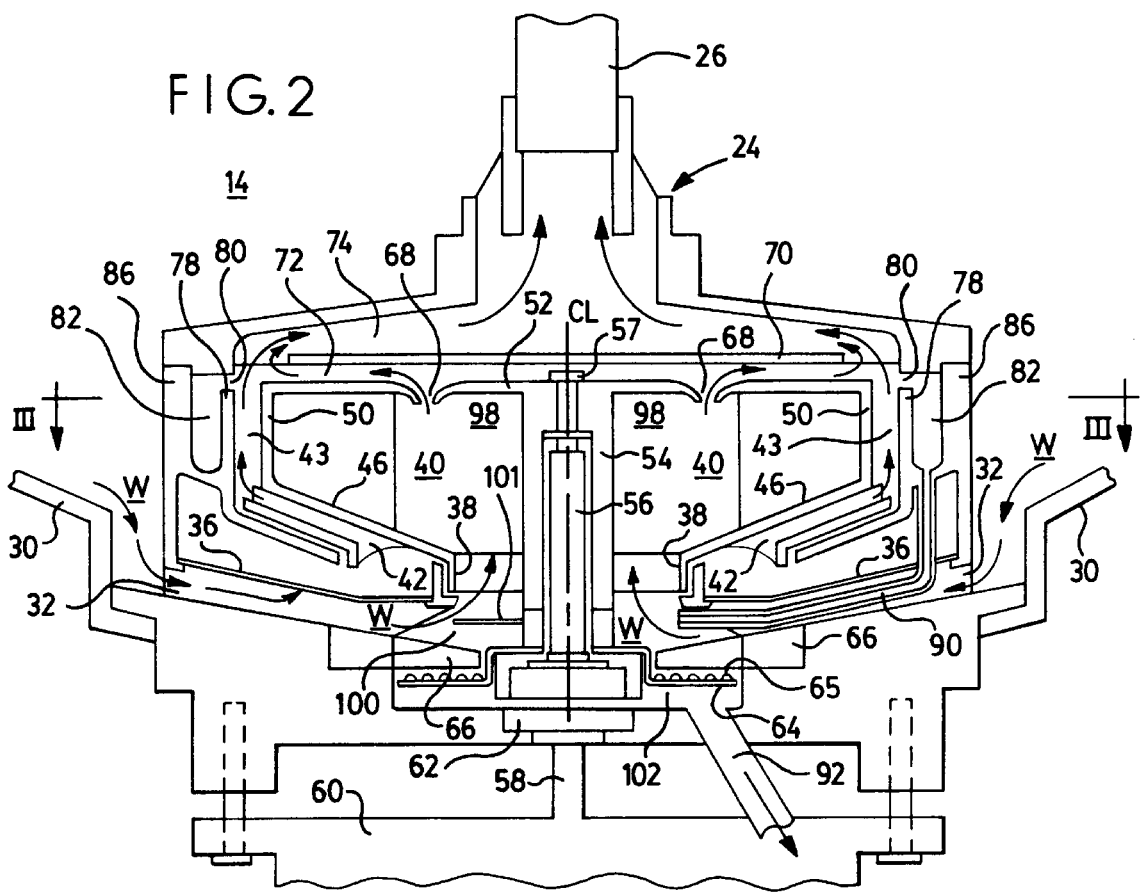
FIG. 2 is a longitudinal sectional view of the soil separator mechanism of FIG. 1.

FIG. 2 shows the soil separator 24 in more detail. The separator 24 is mounted on a floor 30 of the dish compartment 14. Soil laden water W proceeds through an annular gap 32 into the separator 24. A coarse screen 36 is provided in annular form around a center line of the separator 24. Water may proceed through the coarse screen 36 and a first flow rate and also proceed radially inwardly past the screen 36 to a central opening 38 to be drawn into the centrifuge 40 at a second flow rate. Soil laden water W passing through the screen 36 is pumped by centrifugal impeller 42 upwardly as shown.

The impeller 42 is mounted to an inclined annular wall 46 partially defining the centrifuge 40. Inclined annular wall 46 continues to an annular vertical wall 50 which is closed by a disk shaped top wall 52. The disk shaped top wall 52 provides a central hub 54 which is connected by a shaft 56 and screw or bolt 57 to a motor shaft 58 driven by a motor 60. A seal 62 is provided to prevent water within the separator 24 from dripping down onto, for example, the motor or paneling beneath the dishwasher compartment 14. A sizing rotor 64 and/or chopping blade 101 is provided attached to the shaft 56 for rotation therewith. The sizing rotor 64 provides cutting or grating elements 65 which as rotated, grind food particles against stationary vanes 66. The chopping blade 101 provides high velocity impacts on soil to reduce particle size. Reduced size particles from either device proceed out of the drain 92, if operated in a "drain" mode, or allowed to remain in areas 100 and 102 if operated in a "wash" mode, until the system is drained.

Through the disk shaped top wall 52 are arranged a plurality of holes 68 shown coined downwardly which allow water spun within the centrifuge 40 to pass upwardly out of the centrifuge 40. A water distribution diffuser 70 is provided above the hole 68. A passage 72 defined by the top wall 52 and diffuser 70 allows the water to join with the water moved upwardly by the centrifugal impeller 42 and proceed into a plenum 74 flow connected to the pipe 26 for distribution to the water distribution mechanism 18 for spraying the dishes.

The mechanism 18 in all other respects is similar to known dishwasher wash arms. Additionally, if a top mounted upper washer arm is used, a conduit can be employed to flow connect the plenum 74 to a hose leading to the upper wash arm (not shown).

Also, an annular soil concentration wall 78 can be provided surrounding the vertical annular wall 50. Water moved by the centrifugal impeller 42 and influenced by the spinning vertical annular wall 50 allows entrained soil to pass through an annular gap 80 into an annular sump 82 defined between the wall 78 and an outer wall 86 of the mechanism 24. A sump drain line 90 is provided leading from the sump 82 down to the area of the opening 38. Soil accumulated in the sump 82 can be therefore transported down to the separator entrance 38 for collection and confinement.

The centrifugal impeller 42 pumps water through an annular vertical channel 43 upward to supply the pipe 26 with wash water.

Figure 3:
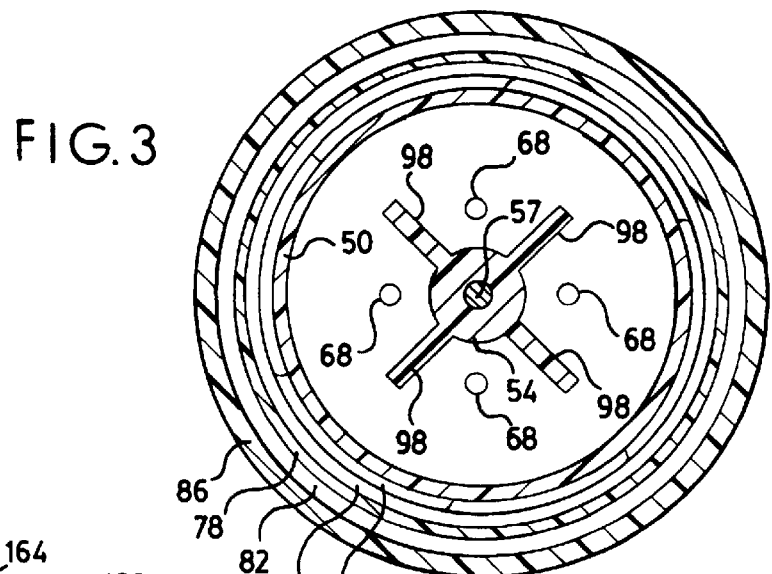
FIG. 3 is a sectional view taken generally along line III—III of FIG. 2.

As shown in FIG. 3, the centrifuge 40 is shown with radially aligned paddles 98 extending from the hub 54 for imparting rotational force to the column of water held within centrifuge 40. The holes 68 are shown which allow the central portion of the water within the centrifuge 40 to leave the centrifuge to pass through the pipe 26 to be recirculated into the dish compartment 14. The size and radial location of the holes 68 can be controlled to further screen soil particles.

In operation, the centrifuge 40 functions on the principle that a spinning column of water with different diameters at each end will pump water. The centrifuge 40 has a smaller diameter at its entrance 38, and a slightly larger diameter defining the location of holes 68. Thus when the motor shaft 58 spins, the connector shaft 56 spins which spins the hub 54. The hub 54 spins the centrifuge walls 52, 50, 46 and the paddles 98 to spin water held within the centrifuge 40. Centrifugal forces separate food soils based on their densities within the centrifuge 40. Heavier than water soils collect on the outer wall of the centrifuge and lighter than water soils collect in the center. By locating the holes 68 at a preselected radial distance from a center line CL of the centrifuge at least equal to radial location of inlet wall 38 to the same centerline CL, relatively clean water can be dispensed out of the holes 68.

To dispose the trapped soils, periodically, the centrifuge 40 is stopped. Some of the heavy food soils may fall out of the centrifuge 40 at this time. By activating the drain system and either allowing the centrifuge 40 to remain stationary, agitate by repeated direction changes, or rotate continuously in either direction, the water and soil will be pumped out of the dishwasher. Whether or not the centrifuge 40 is rotating or in which direction is dependent on the configuration of the soil sizing mechanisms and the type of food soils expected to be handled. In the case of a rotating centrifuge, some food particles and water will remain within the centrifuge after the unit has been pumped dry. At this point in operation, the centrifuge 40 is again stopped and the remaining water and soil should flow downwardly out of the centrifuge down to the sizing and drain area 100. The drain system is again activated to complete the system draining.

The centrifuge 40 is designed to pump water out of the holes 68 at a relatively low flow rate. The centrifugal impeller 42 on the other hand serves to provide a main pumping action for the dishwasher. The impeller 42 draws water across the screen 36 for coarse screening.

Figure 5:
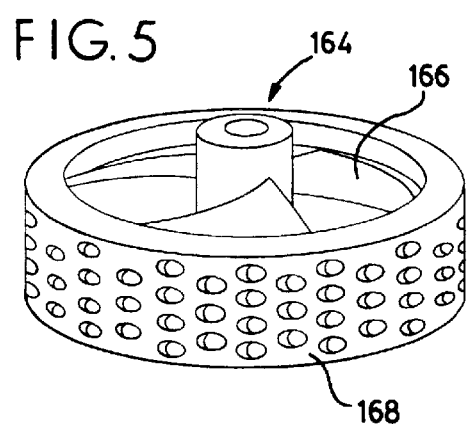
FIG. 5 is a perspective view of the sizing mechanism shown in FIG. 4.
Figure 6:
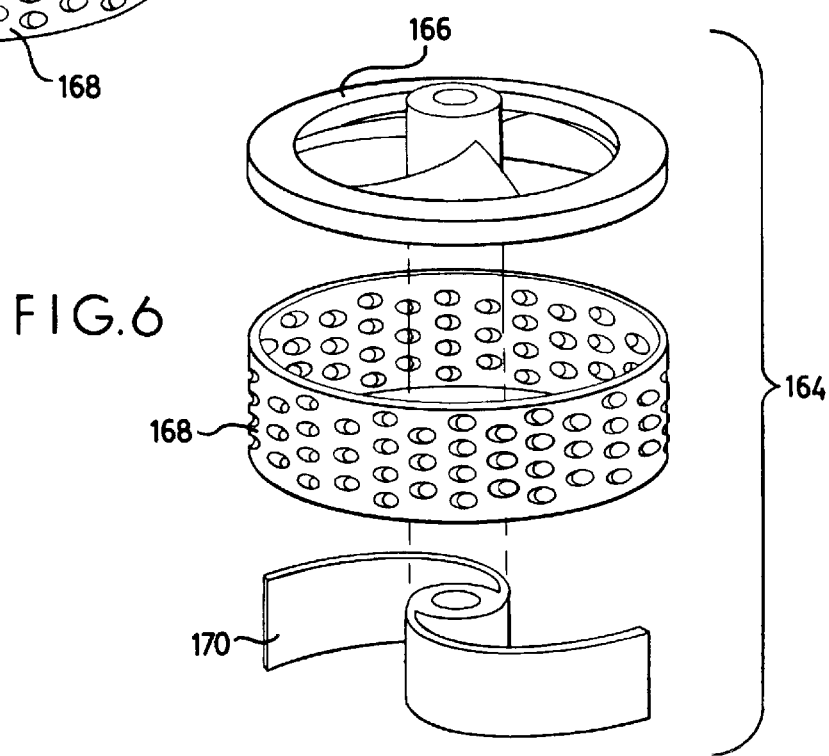
FIG. 6 is an exploded perspective view of the mechanism of FIG. 5.
Figure 4:
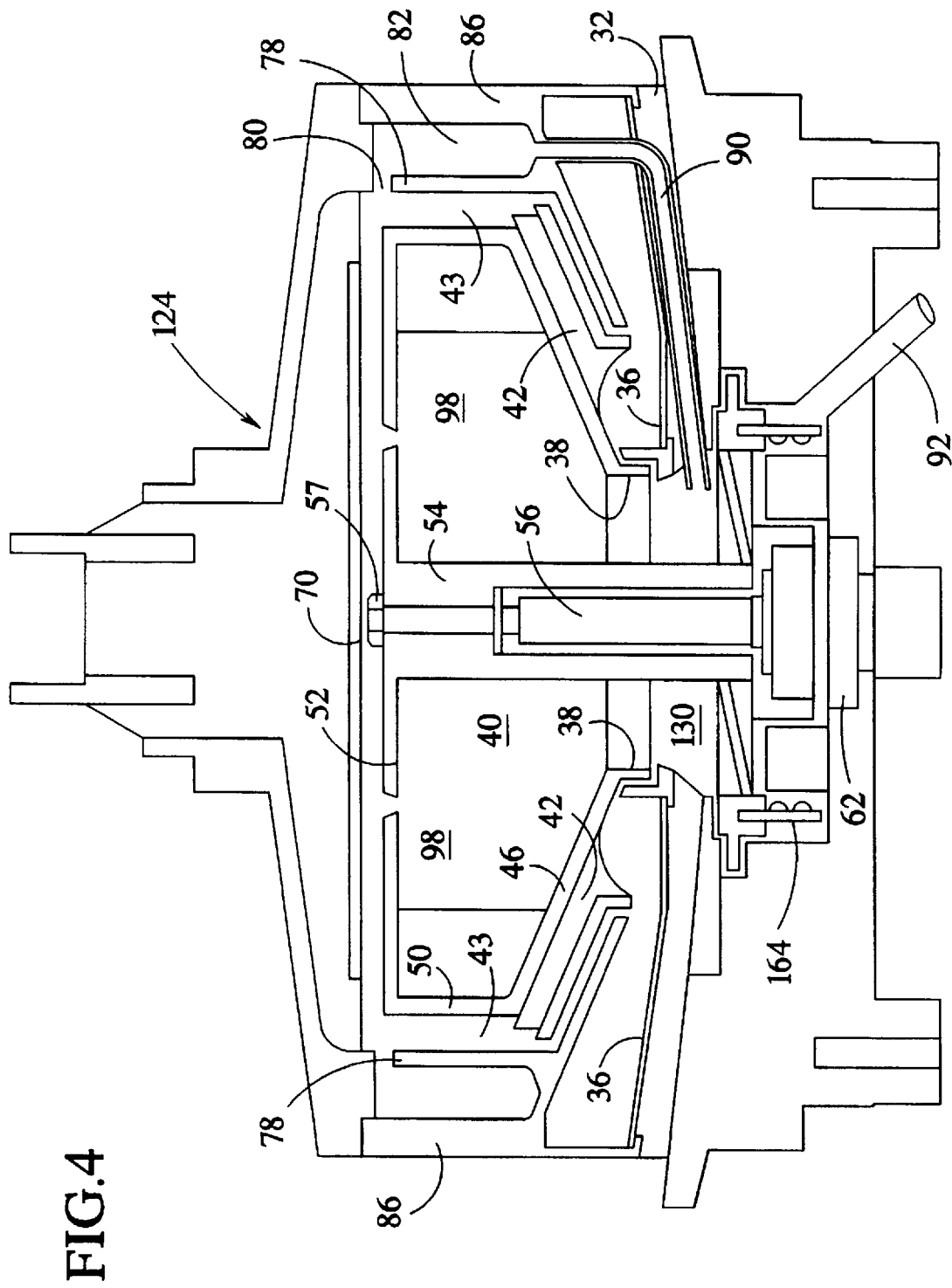
FIG. 4 is a longitudinal sectional view of an alternate embodiment of the separator of FIG. 2.

FIG. 4 describes an alternate embodiment separator 124 having a different soil sizing and drain area 130 including an alternate soil sizing rotor 164. This rotor 164 is shown in detail in FIGS. 5 and 6.

The rotor 164 includes a propeller 166 which when spun in a draining direction encourages flow through the rotor 164 and when spun in a reverse direction (wash direction) prevents flow through the rotor 164. A perforated cylinder 168 is fastened to the propeller 166. The cylinder 168 allows water to pass through to drain during a drain cycle. The cylinder will also chop and size food particles. A spring finger element 170 passes an inside of the cylinder 1 68 to assist in forcing food particles against the cylinder inside surface to effectively grate or grind the particles. The finger elements 170 can be designed to deflect or rotate to prevent stalling the motor if a large hard particle wedges between the finger and the cylinder 168.

Although the present invention has been described with reference to a specific embodiment, those of skill in the art will recognize that changes may be made thereto without departing from the scope and spirit of the invention as set forth in the appended claims.

The embodiments of the invention in which an exclusive property or privilege is claimed are defined as follows:

1. A dishwasher soil separating mechanism, for use in a dish compartment of a dishwasher, the mechanism comprising:
   a housing;
   an entry port in said housing for receiving water recycled from a dish compartment of said dishwasher;
   a centrifuge body mounted for rotation within said housing, having a central hub mounted on a rotational axis thereof, a top wall having at least one aperture therethrough, and an annular side wall closed at a top thereof by said top wall and tapering inwardly and downwardly to a narrower diameter than said top wall, said centrifuge body also having an inlet opening at a bottom thereof within said annular side wall;

a motor means having an output shaft connected to said central hub for spinning said centrifuge body; and wherein said entry port of said housing is in flow communication with said inlet opening at a bottom of said centrifuge body and said at least one aperture in said top wall is in flow communication with an inside of said dish compartment for providing recycled wash water to said dish compartment.

2. The mechanism according to claim 1, further comprising a centrifugal impeller mounted for rotation with said centrifuge, said centrifugal impeller receiving flow from said entry port of said housing and being in flow communication with said dish compartment.

3. The mechanism according to claim 2 further comprising a coarse screen fixed to said housing and arranged between said entry port of said housing and said centrifugal impeller.

4. The mechanism according to claim 3 wherein said coarse screen comprises an annular screen, and further comprising a free-floating scraper ring set on said annular screen for agitating soil settling on said screen.

5. The mechanism according to claim 2 further comprising a soil concentration wall surrounding said annular side wall of said centrifuge body and having a gap on a top side thereof for receiving soil from soil laden water pumped by said centrifugal impeller.

6. The mechanism according to claim 5 further comprising a sizing impeller located below said inlet opening of said centrifuge body, and wherein said gap is in flow communication with an annular sump, and said annular sump provides a drain line for soil connected between said sump and said sizing impeller.

7. The mechanism according to claim 1 wherein said centrifuge body comprises radially arranged paddles spaced apart around an inside circumference of said centrifuge body for moving water being spinned in said centrifuge body in a rotary direction.

8. The mechanism according to claim 1 wherein said annular side wall of said centrifuge body comprises an upper vertical annular wall connected to a lower inclined annular wall extending downwardly and inwardly to said inlet opening, wherein said inlet opening is an annular opening between said inclined annular side wall and said central hub.

9. The mechanism according to claim 1 further comprising a sizing impeller arranged for rotation with said central hub and located below said inlet opening of said centrifuge body.

10. The mechanism according to claim 1 further comprising a diffuser plate mounted above said top wall for forcing water exiting said at least one aperture into a narrow channel extending radially outwardly from said central hub before exiting said separator to said dish compartment.

11. The mechanism according to claim 1 wherein said at least one aperture comprises a plurality of spaced apart apertures arranged at a radial distance from said central hub.

12. A soil separator for removing soil from recycled wash water in a dishwashing apparatus, the separator comprising:
   a soil laden water inlet;
   a recycled water outlet;
   a soil outlet;
   a means for spinning said soil laden water received from said soil laden water inlet, for separating soil from recycled water, the means for spinning comprising a centrifuge having a rotatable hollow body having at least one hole through the top of the hollow body:
   a first means for directing soil from said means for spinning to said soil outlet; and
   a second means for directing recycled water to said recycled water outlet.

13. The separator according to claim 12, wherein said hollow body has a first inside diameter adjacent said soil laden water inlet and a second inside diameter adjacent said recycled water outlet, said second inside diameter larger than said first inside diameter; and said second means for directing recycled water to said recycled water outlet comprises a plurality of holes through the top of said hollow body in communication with said recycled water outlet.

14. The separator according to claim 13, further comprising a centrifugal impeller formed around an outside of said hollow body and in flow communication with said soil laden water inlet and said recycled water outlet.

15. The separator according to claim 18, wherein said first means comprises a sizing impeller arranged beneath said hollow body and above said soil outlet; said sizing impeller rotatable to reduce sizing of soil particles directed to said soil outlet.

* * * * *